(12) United States Patent
D'Arcangelo (10) Patent No.: US 8,499,994 B2
(45) Date of Patent: Aug. 6, 2013

(54) SURGICAL INSTRUMENT AND ACTUATING MOVEMENT TRANSMITTING DEVICE THEREFORE

(75) Inventor: Michele D'Arcangelo, Rome (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 459 days.

(21) Appl. No.: 12/438,774

(22) PCT Filed: Jun. 15, 2007

(86) PCT No.: PCT/EP2007/055957
§ 371 (c)(1),
(2), (4) Date: Oct. 13, 2009

(87) PCT Pub. No.: WO2008/028700
PCT Pub. Date: Mar. 13, 2008

(65) Prior Publication Data
US 2010/0038403 A1    Feb. 18, 2010

(30) Foreign Application Priority Data
Sep. 8, 2006 (EP) ..................................... 06018864

(51) Int. Cl.
*A61B 17/068* (2006.01)
(52) U.S. Cl.
USPC ..................................... 227/179.1; 227/180.1
(58) Field of Classification Search
USPC ................. 227/179.1, 180.1; 600/104; 606/1, 606/159, 219, 142, 153, 205
See application file for complete search history.

(56) References Cited

U.S. PATENT DOCUMENTS

| 5,792,165 | A | 8/1998 | Klieman et al. | |
|---|---|---|---|---|
| 5,807,393 | A * | 9/1998 | Williamson et al. | 606/32 |
| 7,077,856 | B2 * | 7/2006 | Whitman | 606/219 |
| 7,097,650 | B2 * | 8/2006 | Weller et al. | 606/153 |
| 7,810,690 | B2 * | 10/2010 | Bilotti et al. | 227/175.1 |
| 2003/0009441 | A1 | 1/2003 | Holsten et al. | |
| 2006/0191975 | A1 | 8/2006 | Adams et al. | |

FOREIGN PATENT DOCUMENTS

| EP | 1607054 A2 | 12/2005 |
|---|---|---|
| WO | WO 01/91646 A | 12/2001 |
| WO | WO 2006/027014 A | 3/2006 |

OTHER PUBLICATIONS

EPO Search Report dated Oct. 31, 2007 for corresponding patent application, European Patent Application No. PCT/EP2007/055957.
EPO Search Report dated Nov. 14, 2007 for corresponding patent application, European Patent Application No. PCT/EP2007/055957.

* cited by examiner

Primary Examiner — M. Alexandra Elve
Assistant Examiner — Nathaniel Chukwurah (57) ABSTRACT

A surgical instrument, such as a surgical stapling instrument (1), comprises a tissue manipulating portion (2) which is intended to be introduced in the body of a patient, a handle portion (3) with an actuating mechanism (7) adapted to generate actuating movements for the actuation of the tissue manipulating portion (2) and comprising at least a pair of rotary output members (33; 40) and an actuating transmission device (5, 5'; 6, 6') connecting the actuating mechanism (7) of the handle portion (3) to the tissue manipulating portion (2) and comprising at least one pair of rotary rods (17, 17'; 19, 19') for transmitting rotational actuating movements from the pair of rotary output members (33; 40) to the tissue manipulating portion (2). The actuating mechanism (7) comprises synchronization means (31, 32, 32'; 38, 20 39, 39') which link the movements of the two rotary output members (33; 40) of the pair of rotary output members such that they counter-rotate at substantially the same speed.

11 Claims, 7 Drawing Sheets

SURGICAL INSTRUMENT AND ACTUATING MOVEMENT TRANSMITTING DEVICE THEREFORE

The invention relates in general to surgical instruments and in particular to instruments which can be endoscopically introduced in a patients body and which are connected to an extracorporeal handle portion provided with an actuating mechanism by means of dedicated movement transmitting devices adapted to transmit the actuating movements from the handle portion to the surgical instrument inside the body.

With particular reference to a surgical stapling instrument, which can be used, e.g., in the diagnosis and/or therapy of pathologies of the lower gastrointestinal tract, there are two general needs which are hardly reconcilable, i.e. to introduce the surgical stapler as deeply as possible into the natural duct (e.g. colon) in order to reach the region of the pathology which needs to be treated and to control the position and movements of the surgical instrument from outside the body during actuation or, in other words, during the performance of the surgical intervention.

A known surgical stapling instrument, disclosed in WO 01/91646 A1, has a staple fastening assembly located in the distal end region of the stapling instrument, a rigid shaft, and a handle extending from the shaft in the proximal end region of the stapling instrument. This known surgical stapling instrument can be used to excise tissue, e.g. polyps, and to stop bleeding virtually immediately. In a surgical procedure, the stapling instrument is introduced, e.g., into the anal canal and moved to the site of the tissue to be resected. The tissue to be excised can be pulled by means of a separate tissue grasping instrument into the area between an anvil and a cartridge device of the stapler, when the cartridge device and the anvil are in a spaced or open position. Afterwards, the anvil is moved towards the cartridge device in order to clamp the tissue. When the cartridge device and the anvil have reached the closed position, the surgeon can "fire" the instrument, which means that the staples are driven out of the cartridge device, penetrate the tissue, whereupon the ends are bent by the anvil, and a knife or cutting edge is moved towards the anvil in order to cut the tissue. When the instrument is opened, the completely excised tissue can be safely removed from the patient's body together with or prior to removing the instrument itself.

Because of the rigidity and limited length of its insertion shaft, the known surgical stapling instrument enables an excellent stability and control of the position and movements of the staple fastening assembly during actuation but for the same reasons the operational range of the surgical stapling instrument is restricted to an extent that it cannot be used e.g. to excise tissue of the anal canal remote from the rectum.

In order to obviate these drawbacks related to the insertion and deployment of the instrument, a surgical stapling device (disclosed in WO 2006/027014) has been proposed, in which the rigid insertion shaft has been replaced by a flexible shaft which flexibly connects a proximal handle and a distal staple fastening assembly. The flexible shaft, for instance an endoscope, can be considerably long and enables the stapling instrument to be introduced, e.g. into the anal canal, and to be moved forward for a rather long distance to allow for the treatment of tissue at a site remote from the anus. During the introduction and advancement of the stapler, the flexible shaft adapts to the curvature of the intestine.

Even though this solution consents a deeper introduction of the surgical instrument in the patients body, it requires flexibly deformable actuating movement transmitting devices which adapt to the tortuous endoscopic access path and which do not substantially deform or displace in response to actuation. In order to meet these requirements, it has been proposed to use flexible rotary rods which are rotatably mounted in a flexible but torsionally stiff sheath which makes it possible to maintain within certain limits the position of the staple fastening device during actuation and to prevent the staple fastening device from spinning about itself in response to the rotary actuating movement of the rotary rods. These torsionally rigid sheaths, apart from being bulky and having a large bending radius, need to be rigidly coupled to the staple fastening assembly, thereby increasing also the longitudinal dimension of the surgical stapler. This results in a reduced maneuverability of the surgical instrument.

In view of the drawbacks of the prior art surgical instruments and their actuating movement transmitting devices, it is the object of the present invention to provide an actuating movement transmission device for a surgical instrument, e.g. for an endoscopic stapling instrument, which improves and stabilizes the instrument positioning during actuation and at the same time obviates the bulky rigid sheaths and connections thereof.

Within the general scope of the main object, it is a further aim of the present invention to provide a surgical instrument, in particular a surgical stapling device which is equipped with the actuating movement transmission device of the present invention.

These and other problems are solved by an actuating movement transmission device for a surgical instrument (e.g. a surgical stapling device) of the type comprising:
- a tissue manipulating portion (e.g. a staple fastening assembly) which is intended to be introduced in the body of a patient and
- a handle portion with an actuating mechanism adapted to generate actuating movements for the actuation of the tissue manipulating portion, wherein the actuating transmission device is adapted to connect the actuating mechanism of the handle portion to the tissue manipulating portion and comprises at least one pair of rotary rods for transmitting rotational actuating movements from the actuating mechanism to the tissue manipulating portion,
wherein the actuating transmission device comprises synchronization means which link the movements of the two rotary rods of the pair of rotary rods such that they counter-rotate at substantially the same speed.

The object of the invention is also achieved by a surgical instrument (e.g. a surgical stapling device) comprising:
- a tissue manipulating portion (e.g. a staple fastening assembly) which is intended to be introduced in the body of a patient;
- a handle portion with an actuating mechanism adapted to generate actuating movements for the actuation of the tissue manipulating portion and comprising at least a pair of rotary output members;
- an actuating transmission device connecting the actuating mechanism of the handle portion to the tissue manipulating portion and comprising at least one pair of rotary rods for transmitting rotational actuating movements from the pair of rotary output members to the tissue manipulating portion, wherein the actuating mechanism comprises synchronization means which link the movements of the two rotary output members of the pair of rotary output members such that they counter-rotate at substantially the same speed.

The object of the invention is further achieved by a method of operating a surgical instrument (e.g. a surgical stapling device) of the type comprising:

a tissue manipulating portion (e.g. a staple fastening assembly) which is intended to be introduced in the body of a patient;

a handle portion with an actuating mechanism adapted to generate actuating movements for the actuation of the tissue manipulating portion;

an actuating transmission device connecting the actuating mechanism of the handle portion to the tissue manipulating portion and comprising at least one pair of rotary rods for transmitting rotational actuating movements from the actuating mechanism to the tissue manipulating portion, wherein the method comprises the step of moving the two rotary rods of the pair of rotary rods in a synchronized manner such that they counter-rotate at substantially the same speed.

Thanks to the synchronized rotation of the two rotary rods in counter directions and at substantially the same (preferably exactly the same) rotational speed, the torque acting on the tissue manipulating portion is balanced thereby preventing undesired rotation and obviating cumbersome torsional stiffening structures.

According to an aspect of the present invention, the surgical instrument is a surgical stapling instrument comprising:

a staple fastening assembly in the distal end region of the instrument, including a curved cartridge device comprising at least one curved open row of staples having a concave side and a convex side and, opposite to the cartridge device, a curved anvil having a staple forming face and being adapted to cooperate with the cartridge device for forming the ends of the staples exiting from the cartridge device, an anvil moving device arranged at the staple fastening assembly and adapted to move the anvil with respect to the cartridge device from a spaced position for positioning tissue therebetween to a closed position for clamping the tissue, a staple driving device arranged at the staple fastening assembly and adapted to drive the staples out of the cartridge device towards the anvil, a handle portion arranged in the proximal end region of the instrument and operatively connected to the staple fastening assembly, the handle portion housing the actuating mechanism which is adapted to generate an anvil actuating movement of a pair of first rotary output members and a staple actuating movement of a pair of second rotary output members;

two first rotary rods connected to the two first rotary output members and to the anvil moving device for transmitting said anvil actuating movement thereto;

two second rotary rods connected to the two second rotary output members and to the staple driving device for transmitting said staple actuating movement thereto, wherein the synchronization means comprise:

first synchronization means which link the movements of the two first rotary output members such that they counter-rotate at substantially the same speed.

second synchronization means which link the movements of the two second rotary output members such that they counter-rotate at substantially the same speed.

In accordance with an embodiment of the invention, the synchronization means comprise a gear mechanism, preferably a double sided frontal or bevel drive gear meshing with two oppositely arranged parallel driven pinions which counter rotate at the same speed upon rotation of the double sided drive gear.

Within the present description, the term "staple" is used in a very general sense. It includes metal staples or clips, but also surgical fasteners made of synthetic material and similar fasteners. Synthetic fasteners usually have a counterpart (retainer member) held at the anvil. In this sense, the terms anvil and staple forming face also have a broad meaning which includes, in the case of two-part synthetic fasteners, the anvil like tool and its face where the retainer members are held, and similar devices.

These and other details and advantages of the present invention shall be made apparent from the accompanying drawings and the description thereof, which illustrate embodiments of the invention and, together with the general description of the invention given above, and the detailed description of the invention given below, serve to explain the principles of the present invention.

Figure 1:
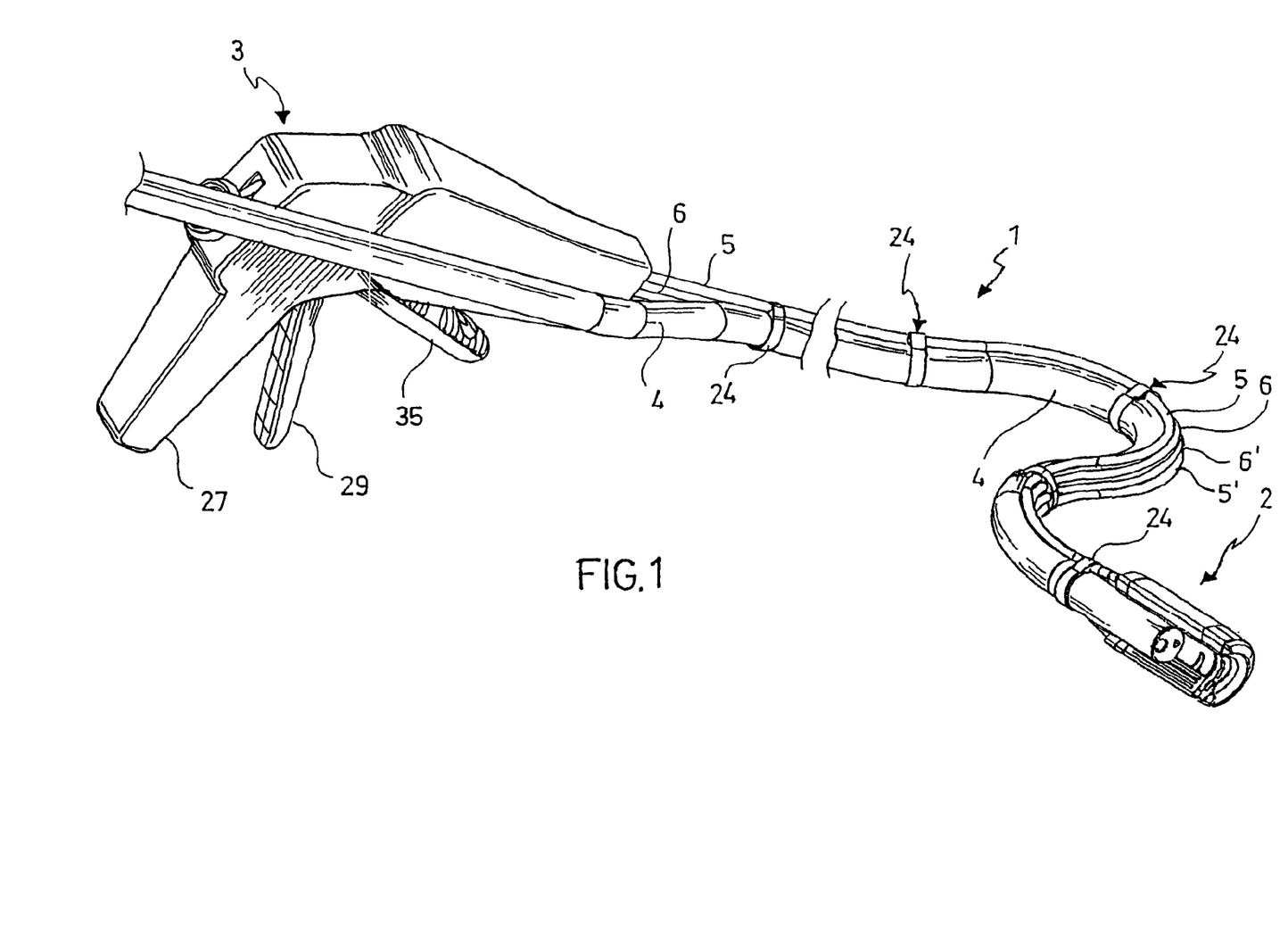
FIG. 1 is a isometric view of a surgical stapling instrument according to an embodiment of the invention.
Figure 2:
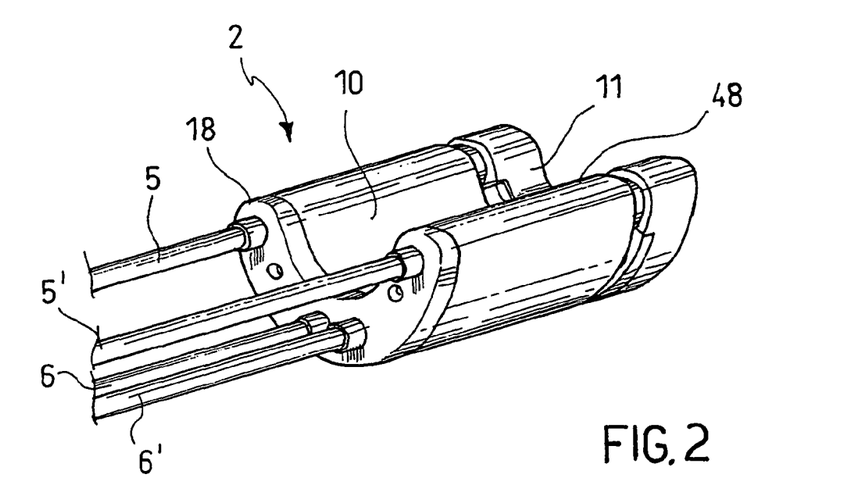
FIG. 2 is a proximal isometric view of a tissue manipulating portion of the instrument in FIG. 1.
Figure 3:
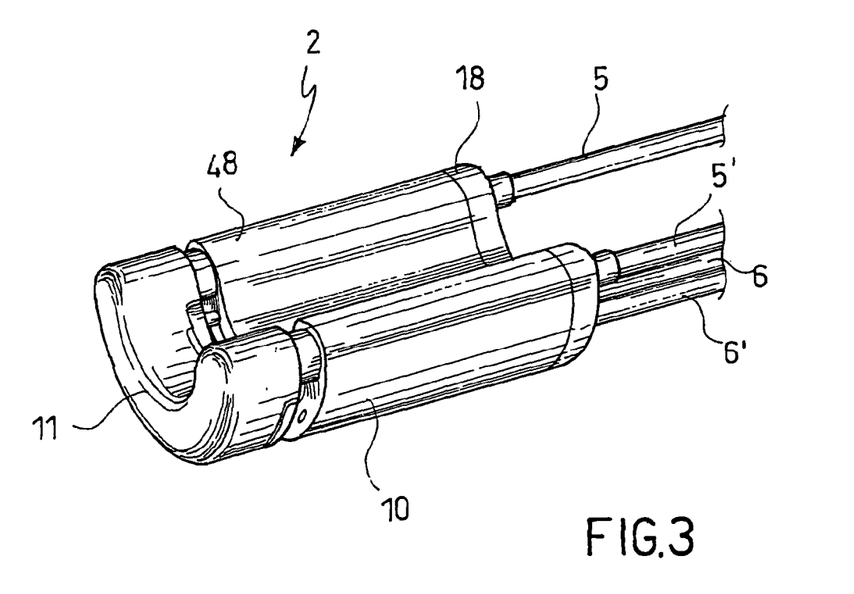
FIG. 3 is a distal isometric view of the tissue manipulating portion of the instrument in FIG. 1.

Turning to the figures, FIG. 1 is an isometric overall view of a surgical stapling instrument 1 according to an embodiment of the invention. The stapling instrument 1 comprises, in its distal end region, a staple fastening assembly 2 and, in its proximal end region, a handle 3. The handle 3 and the staple fastening assembly 2 are connected via an elongate rigid or preferably flexible insertion shaft, e.g. an endoscope 4 which serves as a flexible backbone and provides structural strength to the instrument 1. A first pair of elongate actuating movement transmitters 5, 5' and a second pair of elongate actuating movement transmitters 6, 6' connect an actuating mechanism 7 housed in the handle 3 to an anvil moving device 8 and to a staple drive device 9 of the staple fastening assembly 2 for transmitting actuating movements from the actuating mechanism 7 to the staple fastening assembly 2 in order to perform the functions of the stapling instrument 1.

The main components of the staple fastening assembly 2 are a cartridge device 10, which contains several curved open rows of staples as well as a knife or cutting edge, and a curved anvil 11, which has a staple forming face and is adapted to cooperate with the cartridge device 10 to form the ends of the staples expelled from the cartridge device when the stapling instrument 1 is "fired".

The anvil 11 can be moved with respect to the cartridge device 10 in a parallel relationship, i.e. in a direction parallel to a longitudinal axis X of the staple fastening assembly 2. In the views of FIGS. 5 and 6, the anvil 11 is spaced apart from the cartridge device 10, while in FIGS. 4 and 7, the same anvil 11 has been entirely moved towards the cartridge device 10. As already explained, the mechanism and its components for moving anvil 11 relative to the cartridge device 10 are generally referred to as (anvil) moving device 8, whereas the mechanism and the components for expelling the staples are generally referred to as (staple) driving device 9.

The anvil 11 comprises two proximally extending parallel arms 14 which are preferably arranged at two opposite lateral ends 15 of the anvil 11. Each arm 14 is slidably received in a guided manner in one of two guide seats 16 formed preferably near two opposite lateral ends of the cartridge device 10 in order to impose the movement track of the anvil 11 with respect to the cartridge device 10.

The moving device 8 comprises a first pair of two moving screws 17, 17', each one of which is received in a rotatably free but axially stationary manner in apposite seats defined in a proximal base structure 18 of the staple fastening assembly 2 and in axial alignment with respectively one of the two anvil arms 14. The distally extending threaded shafts of the moving screws 17, 17' fit into corresponding threaded holes extending into longitudinal direction inside the arms 14 such that a rotation of the moving screws 17, 17' causes the anvil arms 14 together with the anvil 11 to translate along the moving screws 17, 17' with respect to the cartridge device 10.

Similarly, the staple driving device 9 comprises a second pair of two driving screws 19, 19', each one of which is received in a rotatably free but axially stationary manner in apposite seats defined in the proximal base structure 18 of the staple fastening assembly 2 and in thread-engagement with corresponding threaded holes defined in a pusher base 20 such that a rotation of the driving screws 19, 19' causes the pusher base 20 to translate along the driving screws 19, 19' (in the longitudinal direction X of the staple fastening assembly 2) with respect to the base structure 18, the anvil 11 and a cartridge 21 containing the staples. As is known, the movement of the pusher base 20 which acts directly or indirectly on the staples and, preferably, also on a knife (not shown or hidden in the figures) causes the expulsion of the staples and the advancement of the knife towards and against the staple forming surface of the anvil.

To this end, the pusher base 20 may support (via an intermediate part) a pusher platform from which a plurality of pusher fingers extend longitudinally. Each of the pusher fingers supports a staple such that the pointed ends of the staples are aligned in distal direction. The pusher fingers and the related staples are guided in individual slots formed in the housing of the cartridge 21. Moreover, the intermediate part supports the preferably arcuate knife which has a concave side, a convex side opposite to the concave side and a distal cutting edge.

A staple forming face 25 which is provided on the anvil 11 is preferably made of metal and comprises e.g. three rows of staple forming depressions, which are aligned to the pointed ends of staples 26. Moreover, a knife depression (hidden in the figures) is provided in the proximal end face of the anvil 11, which is aligned to the cutting edge of the knife and preferably filled with a plastics material which acts as a cutting block but can be cut through by the knife in a way to indicate the performance of a complete cut through the tissue.

According to a preferred embodiment, the two moving screws 17, 17' of the first pair are arranged at two opposite lateral ends of the staple fastening assembly and the two driving screws 19, 19' of the second pair are arranged side by side centrally between the moving screws 17, 17' defining together with the latter a symmetrical screw pattern with respect to a longitudinal central plane of the curved staple fastening assembly 2.

Due to the provision of synchronization means which will be described below, the pair of moving screws 17, 17' can be rotated only at the same rotational speed and in counter direction, thereby balancing and compensating the torsional input and the rotational inertial effects acting on the staple fastening assembly 2 during the anvil approximation movement.

Similarly, synchronization means are provided that constrain also the pair of driving screws 19, 19' to rotate at the same rotational speed and in counter direction, thereby balancing and compensating the torsional input and the rotational inertial effects acting on the staple fastening assembly 2 due to the firing of the instrument 1.

In the exemplary embodiment, the knife driving device is advantageously coupled with the staple driving device 9 but, alternatively, a distinct knife driving device can be provided which is drivable by two screw drives which are also preferably constrained to rotate at the same rotational speed and in counter direction in order to balance the torsional and rotational inertial effects on the staple fastening assembly during cutting.

The first pair of movement transmitters 5, 5' comprises a pair of rotary rods 12 (FIG. 10) each of which is preferably rotatably mounted in a flexible sheath 22. In the embodiment, the rotary rods 12 are single flexible structures all along. Different designs, e.g. a structure comprising flexibly linked short rigid members or a tightly wound helix are conceivable, too. At their distal ends, each of the two rotary rods 12 is attached in a torque transmitting manner, via a connector, to a proximal end of respectively one of the two (anvil) moving screws 17, 17'.

In a similar way, also the second pair of movement transmitters 6, 6' comprises a pair of rotary rods 13 (FIG. 10) each of which is preferably rotatably mounted in a flexible sheath 23. In the embodiment, the rotary rods 13 are single flexible structures all along. Different designs, e.g. a structure comprising flexibly linked short rigid members or a tightly wound helix are conceivable, too. At their distal ends, each of the two rotary rods 13 is attached in a torque transmitting manner, via a connector, to a proximal end of respectively one of the two (staple) driving screws 19, 19'.

The above mentioned synchronization means acts directly or indirectly on each of the two pairs of first 12 and second 13 rotary rods in a way that the first rotary rods 12 rotate at the same rotational speed and in counter direction when they transmit an anvil approximating actuating movement and that the second rotary rods 13 rotate at the same rotational speed and in counter direction when they transmit a staple driving actuating movement from the handle actuating mechanism to the staple fastening assembly 2.

In the embodiment illustrated in FIG. 1, the two pairs of movement transmitters 5, 5', 6, 6' are attached to the insertion shaft (endoscope 4) by means of a plurality of spaced holders 24. Each holder has a lock for attaching the holder in an annular configuration around the insertion shaft 4 and recesses for accommodating the movement transmitters 5, 5', 6, 6'. In accordance with an embodiment, the lock comprises a dove tail shaped protrusion and a notch fitting thereto in order to enable a reversible shape lock of the holder.

Alternatively, the movement transmitters could be housed partially or totally inside a flexible or rigid insertion shaft.

The mechanical connection between the flexible insertion shaft 4 and the staple fastening assembly 2 or the handle 3 can be entirely accomplished by means of the holders 24 and the pairs of actuating movement transmitters 5, 5', 6, 6'. In particular in the area of handle 3, the flexibility of this design, with no rigid attachment of the handle 3 to the endoscope (acting as insertion shaft), can be advantageous. In the distal end region of stapling instrument 1, the endoscope 4 may be additionally fixed to the cartridge device 10 of the staple fastening assembly 2, e.g. by bonding.

Figure 9:
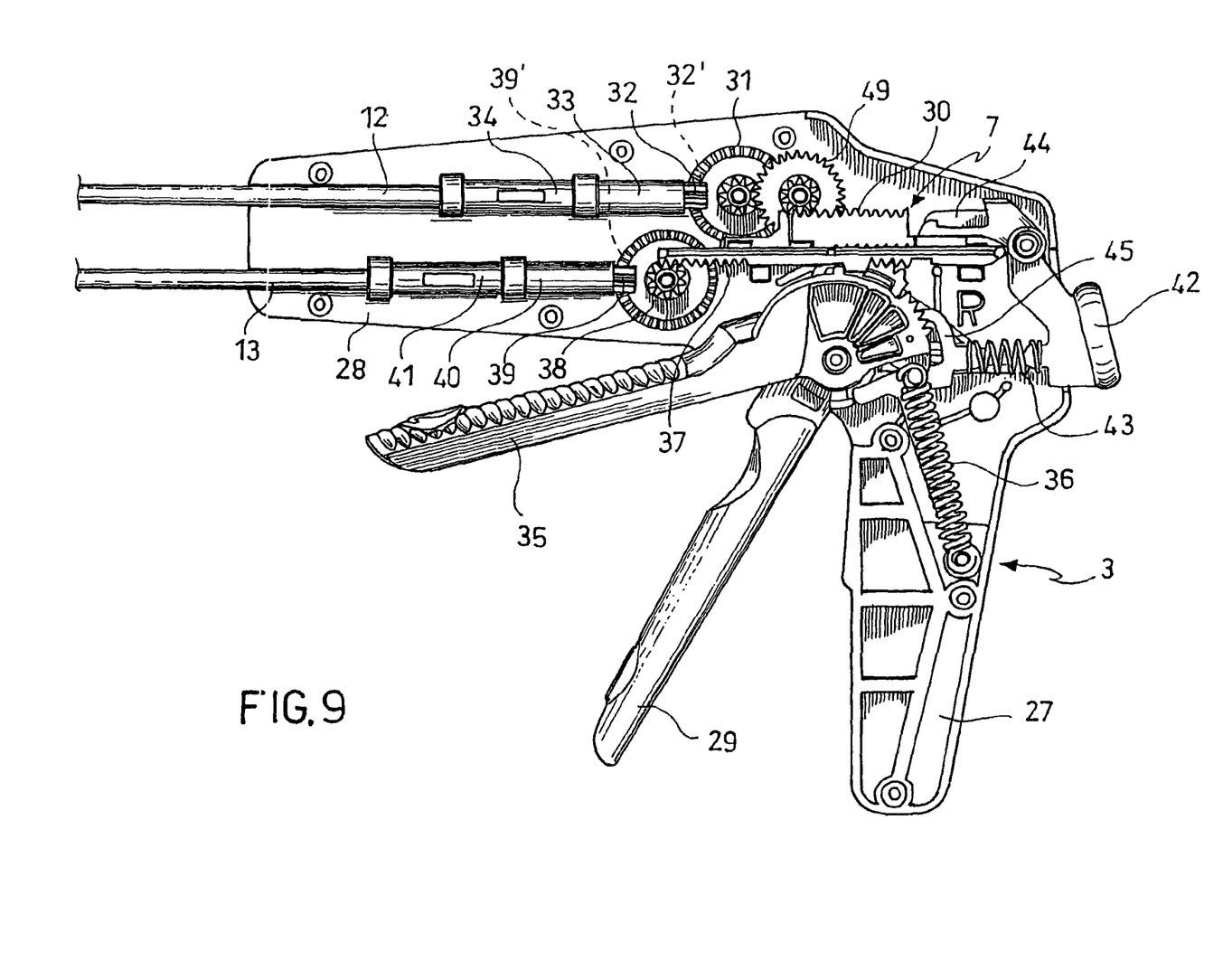
FIG. 9 is a side view of an opened handle portion and an internal actuating mechanism of the surgical stapling instrument in FIG. 1.
Figures 10, 11, 12:
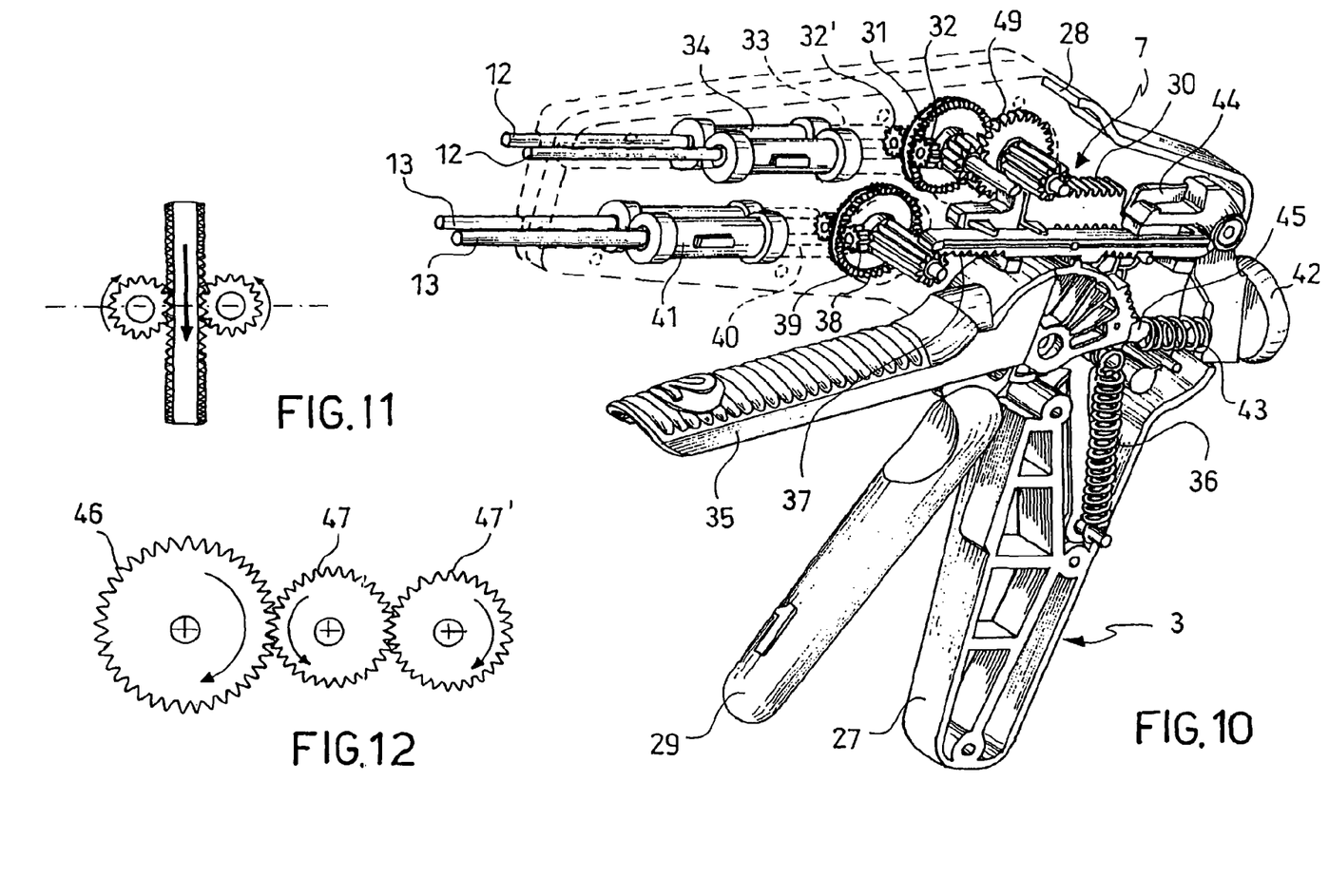
FIG. 10 is an isometric lateral view of the opened handle portion and the internal actuating mechanism of the surgical stapling instrument in FIG. 1.
FIGS. 11 and 12 are schematic illustrations of two embodiments of a rotary movement synchronization device of the surgical stapling instrument according to the invention.

FIGS. 9 and 10 illustrate the internal actuating mechanism 7 of the handle 3. Handle 3 comprises a grip 27 designed to rest in the operator's palm and a gear housing 28.

An anvil actuating member 29 is part of the (anvil) moving device 8. When the anvil actuating member 29, preferably a swivellably mounted lever, is moved towards grip 27, a rack 30 shifts in distal direction and rotates, via intermediate gear 48, gear 31. In the embodiment, gear 31 is a double sided frontal or bevel gear having two opposite tooth rows formed on each side thereof. Each of the opposite tooth rows meshes with one of two parallel pinions 32, 32', thereby changing the direction of the rotational axis by 90° and constraining the movement of the two pinions 32, 32' to a counter rotation at the same speed. The pinions 32, 32' are rotationally coupled to a pair of first rotary output members (rotary rod portions) 33 which are supported by bearings 34 and which are rotationally coupled or which can be removably rotationally coupled to the proximal ends of the first rotary rods 12 for piloting the anvil movement.

Hence, upon pressing the anvil actuating member 29, the rotary rods 12 of the first movement transmitters 5, 5' are caused to a synchronized rotary movement in counter direction and at the same speed about their longitudinal axes. Because of the gear ratio provided by gear 31 and pinions 32, 32', this synchronized counter-rotational movement is relatively fast.

In a similar way, upon pressing a swivellably mounted staple actuating member 35 against the force of a spring 36 ("firing" the instrument), a rack 37 shifts in distal direction and drives a double sided frontal or bevel gear 38 meshing with two pinions 39, 39', thereby changing the direction of the rotational axis by 90° and constraining the movement of the two pinions 39, 39' to a counter rotation at the same speed. The pinions 39, 39' are rotationally coupled (in the sense of a coupling adapted to transmit rotation) to a pair of second rotary output members (rotary rod portions) 40 which are supported by bearings 41 and which are rotationally coupled or which can be removably rotationally coupled to the proximal ends of the second rotary rods 13 for piloting the staple driving device.

In order to release (retract) the staple driving device after the staples have been applied, a release button 42 has to be pressed against the force exerted by a spring 43. After "firing" and before pressing release button 42, a catch 44 engages a protrusion of the staple driving actuating mechanism and keeps rack 37 in a distal position. Moreover, rack 30 is held forward and in place by this mechanism as well, while staple actuating member 35 is pressed. Pressing release button 42 lifts the catch 44, which releases the protrusion of the staple driving actuating mechanism such that, via the action of spring 36, rack 37 returns to its original proximal position.

According to an embodiment, a safety feature (not shown in detail) comprises a pin held by a part 45 until part 45 is pushed out of the way upon actuation of anvil actuating member 29. This ensures that staple actuating member 35 cannot be used prior to anvil actuating member 29.

As will be immediately appreciated by those skilled in the art, the double sided frontal or bevel gears meshing with the two parallel pinions (FIGS. 10 and 11) provide the above mentioned means for synchronizing the movement of the pairs of rotary rods and of the pairs of driving screws and moving screws, respectively, such that they rotate in counter direction and at the same rotational speed, thereby obtaining the balancing of the torsional input and rotational inertia acting on the staple fastening assembly during actuation.

FIG. 12 illustrates one of further possible embodiments of such synchronization means comprising driving (spur) gear 46 meshing with a first driven pinion 47 of a pair of driven pinions 47, 47' having the same diameter and number of teeth. The first pinion 47 meshes in turn with the second pinion 47' such that, upon rotation of the driving spur gear 46, the couple of driven pinions 47, 47' rotate at the same speed but in counter direction. Of course, it is not the intention of the inventors to limit the scope of the present invention to such specific embodiments of the synchronization means which have been described as advantageous, but not limiting examples.

In the illustrated embodiment, such synchronization means are provided in the actuating mechanism arranged in the handle of the instrument. Similarly, the synchronization means can be provided at the actuating movement transmitters 5, 5', 6, 6' and act on the pairs of rotary rods 12, 13 and/or they might be provided at or integrated in the staple fastening assembly 2 and act directly on the pairs of anvil moving screws 17, 17' and or staple driving screws 19, 19'.

Figure 4:
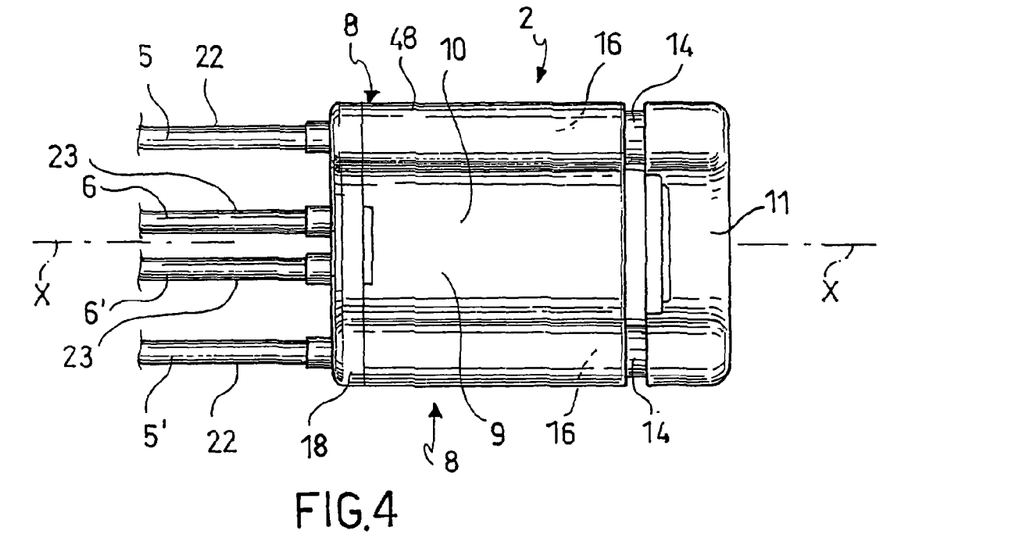
FIG. 4 is a lateral view of the tissue manipulating portion in a fully closed configuration.
Figure 5:
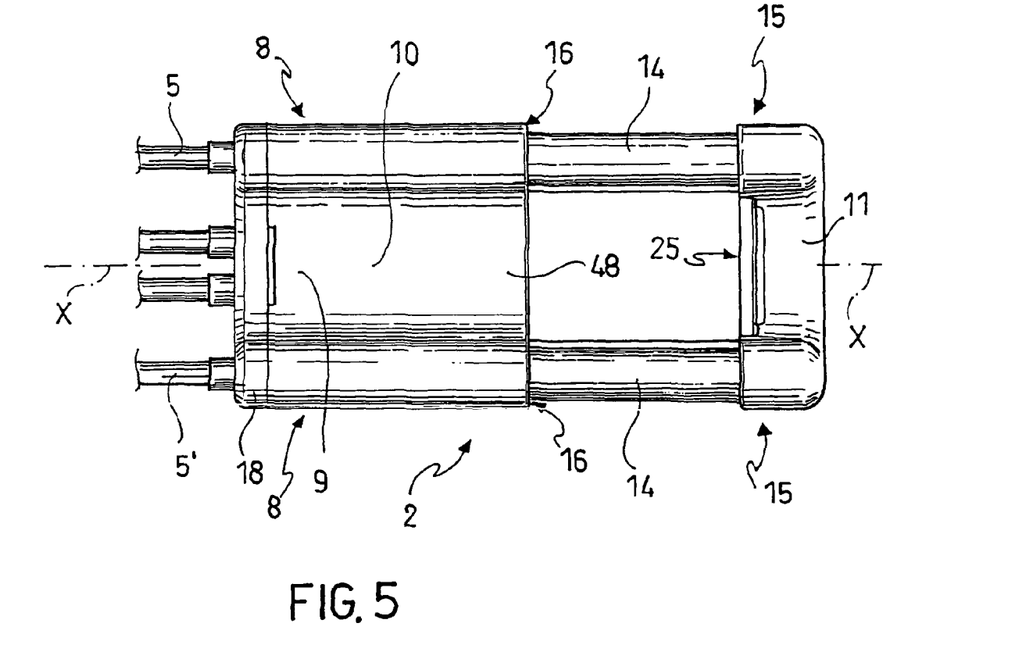
FIG. 5 is a lateral view of the tissue manipulating portion in a fully opened configuration.
Figure 6:
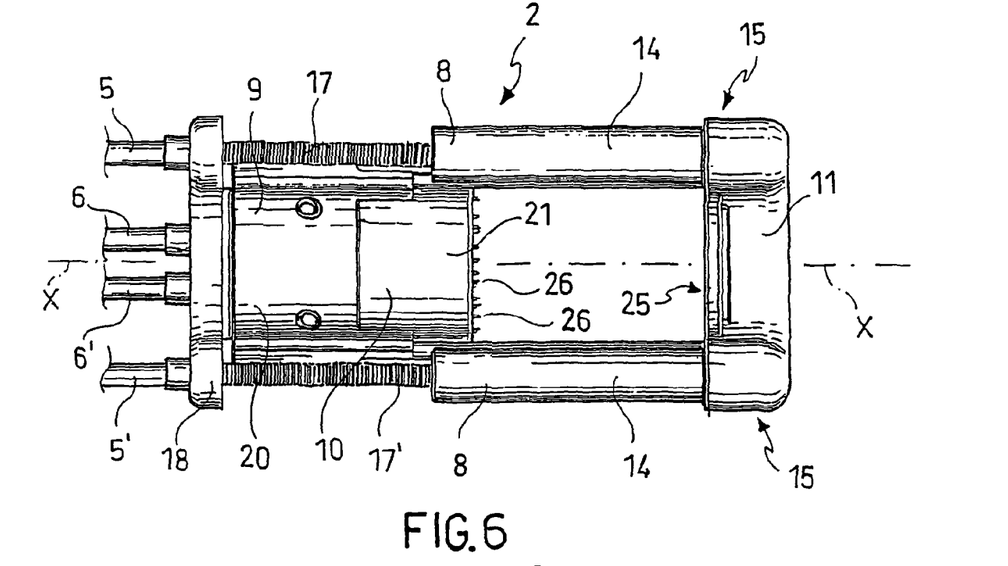
FIG. 6 is a lateral view of the tissue manipulating portion with an outer casing being removed in order to show a pair of anvil moving screws.
Figure 7:
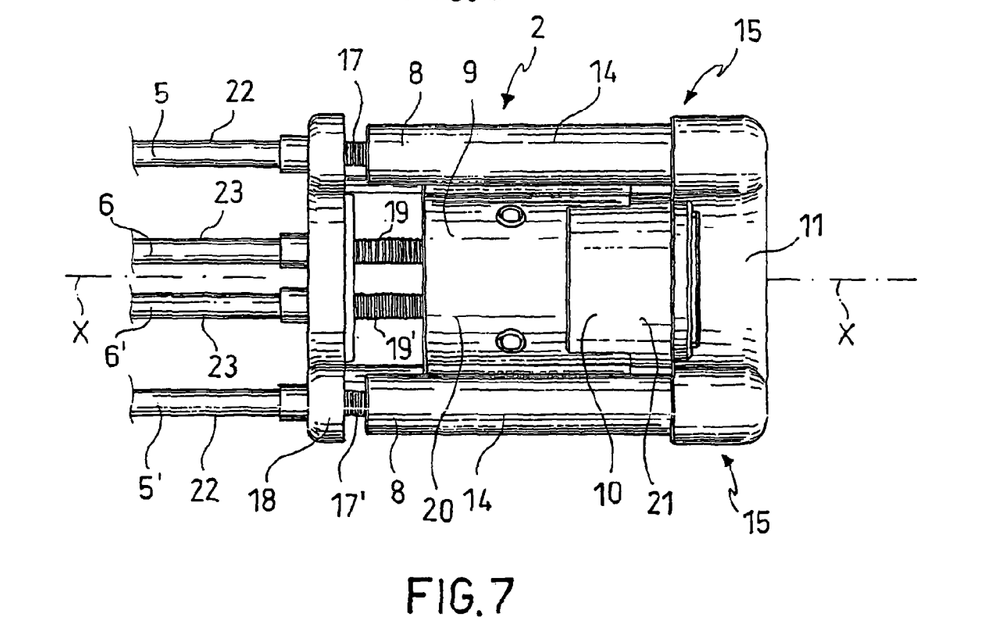
FIG. 7 is a lateral view of the tissue manipulating portion with an outer casing being removed in order to show a pair of staple driving screws.
Figure 8:
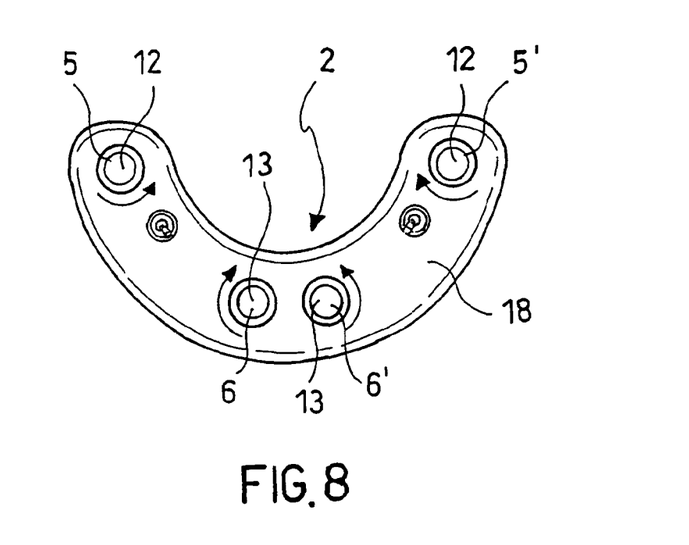
FIG. 8 is a proximal end view of the tissue manipulating portion illustrating the direction of input torque of two pairs of actuation movement transmitters.

FIGS. 4 and 5 are similar to FIGS. 6 and 7, but the cartridge device 10 has been completed by an outer casing 48. In the embodiment, the casing 48 comprises an injection-molded part made of medical grade plastics material. FIGS. 5 and 6 illustrate the configuration in which the anvil 11 has been moved distally to a spaced position, i.e. to a position in which the distance between the cartridge device 10 and the staple forming face 25 of the anvil 11 is large. This corresponds to a large exposed area of the (anvil) moving screws 17, 17' in FIG. 6. In this spaced position, tissue of a patient to be excised can be pulled between the staple forming face 25 of anvil 11 and the cartridge device 10. Thereafter, anvil actuating member 29 of the moving device is pressed towards grip 27, which causes a counter rotational movement at the same speed of both first rotary rods 12 and both anvil moving screws 17, 17', resulting in a shift of the anvil 11 in proximal direction, thereby balancing and compensating the input torque and rotational inertia acting on the staple fastening assembly 2 whose position remains stable. In this way, the anvil 11 reaches a closed position and the tissue is clamped.

The next step of the procedure is shown in FIGS. 4 and 7 (in FIG. 7 the casing 48 is removed). As explained, the anvil 11 has been moved to a closed position, which is evident from a small exposed area of the two anvil moving screws 17, 17'. Moreover, staple actuating member 35 has been pressed, which causes a counter rotational movement at the same speed of both second rotary rods 13 and both staple driving screws 19, 19', resulting in a longitudinal movement in distal direction of the pusher base 20, thereby balancing the input torque and rotational inertia acting on the staple fastening assembly 2 whose position remains stable.

The pusher base 20 (and, if provided, the intermediate part, the pusher platform, the pusher fingers) move the staples 26 and the knife, wherein the cutting edge of the knife follows the pointed ends of the staples 26. In this way, the staples are driven out of the cartridge against the staple forming face 25 which form the pointed staple ends, as known.

After the tissue has been stapled, it is cut and excised by the knife. In this way, the tissue to stay with the patient is safely stapled by at least one, preferably two rows of staples on the convex side of the knife, which immediately stops bleeding, whereas the part of the tissue to be removed from the patient is stapled and held together by at least one row of staples. After stapling, release button 42 is pressed, such that rack 37 and actuating member 35, by means of the force exerted by spring 36, return to their original positions. Additionally, this effects a reverse motion of the moving device, increasing the distance between the anvil 11 and the cartridge device 10 in order to release the clamped tissue and to be able to remove the stapling instrument 1 from the patient. The excised portion of the tissue might remain in the staple fastening assembly 2 during removal.

While the present invention has been illustrated by description of several embodiments and while the illustrative embodiments have been described in considerable detail, it is not the intention to restrict or in any way limit the scope of the appended claims to such detail. Additional advantages and modifications may readily appear to those skilled in the art.

Figure 13:
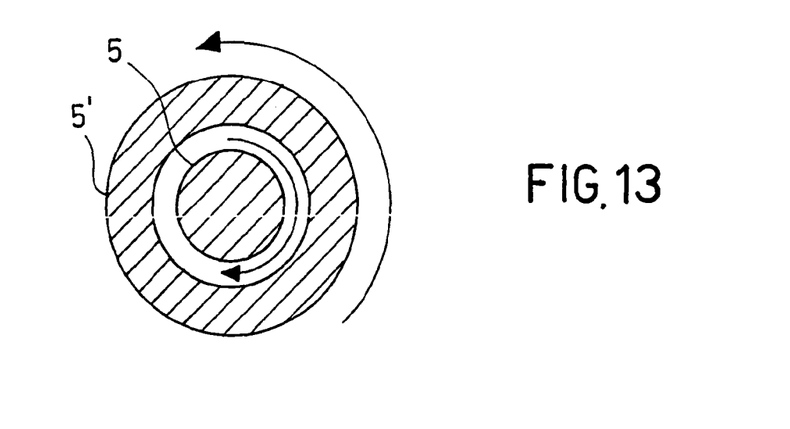
FIG. 13 is a schematic illustration of an alternative embodiment of a detail of the device and instrument according to the invention.

For instance, the pair of counter rotating output members, rotary rods, anvil moving screws and/or staple driving screws need not necessarily be embodied by two parallel spaced apart members, but can comprise two coaxially arranged (e.g. inserted in one another) counter rotating members, rods or screws or screw shafts, as schematically illustrated in FIG. 13.

What is claimed is:

1. An actuating movement transmission device for a surgical instrument of the type comprising:
   a tissue manipulating portion which is intended to be introduced in the body of a patient and
   a handle portion with an actuating mechanism adapted to generate actuating movements for the actuation of the tissue manipulating portion,
   wherein the actuating transmission device is adapted to connect the actuating mechanism of the handle portion to the tissue manipulating portion and comprises at least one pair of rotary rods for transmitting rotational actuating movements from the actuating mechanism to the tissue manipulating portion,
   wherein the actuating transmission device comprises synchronization means which constrain the two rotary rods such that, in response to said actuating movements, the two rotary rods rotate both contemporaneously with respect to said handle portion about parallel rotation axes at substantially same rotational speeds but in opposite senses of rotation.

2. A method of operating a surgical instrument of the type comprising:
   a tissue manipulating portion which is intended to be introduced in the body of a patient;
   a handle portion with an actuating mechanism adapted to generate actuating movements for the actuation of the tissue manipulating portion;
   an actuating transmission device connecting the actuating mechanism of the handle portion to the tissue manipulating portion and comprising at least one pair of rotary rods for transmitting rotational actuating movements from the actuating mechanism to the tissue manipulating portion,
   wherein the method comprises the step of constraining the two rotary rods of the pair of rotary rods such that, in response to said actuating movements, the two rotary rods rotate both contemporaneously with respect to said handle portion about parallel rotation axes at substantially same rotational speeds but in opposite senses of rotation.

3. A surgical instrument, comprising:
   a tissue manipulating portion which is intended to be introduced in the body of a patient;
   a handle portion with an actuating mechanism adapted to generate actuating movements for the actuation of the tissue manipulating portion and comprising at least a pair of two rotary output members;
   an actuating transmission device connecting the actuating mechanism of the handle portion to the tissue manipulating portion and comprising at least one pair of two rotary rods for transmitting rotational actuating movements from the pair of two rotary output members to the tissue manipulating portion,
   wherein the actuating mechanism comprises synchronization means which constrain the two rotary output members such that, in response to said actuating movements, the two rotary output members rotate both contemporaneously with respect to said handle portion about parallel rotation axes at substantially same rotational speeds but in opposite senses of rotation.

4. A surgical instrument according to claim 3, being a surgical stapling instrument, comprising:
   a staple fastening assembly in the distal end region of the instrument, including a cartridge device comprising at least one row of staples and, opposite to the cartridge device, an anvil having a staple forming face and being adapted to cooperate with the cartridge device for forming the ends of the staples exiting from the cartridge device,
   an anvil moving device arranged at the staple fastening assembly and adapted to move the anvil with respect to the cartridge device from a spaced position for positioning tissue therebetween to a closed position for clamping the tissue,
   a staple driving device arranged at the staple fastening assembly and adapted to drive the staples out of the cartridge device towards the anvil,
   a handle portion arranged in the proximal end region of the instrument and operatively connected to the staple fastening assembly, said handle portion housing said actuating mechanism which is adapted to generate and apply an anvil actuating movement to a pair of first rotary output members and to generate and apply a staple actuating movement to a pair of second rotary output members;
   two first rotary rods connected to the two first rotary output members and to the anvil moving device for transmitting said anvil actuating movement thereto;
   two second rotary rods connected to the two second rotary output members and to the staple driving device for transmitting said staple actuating movement thereto,
   wherein said synchronization means comprise:
   first synchronization means which constrain the two first rotary output members such that, in response to said anvil actuating movement, the two first rotary output members rotate both contemporaneously with respect to said handle portion about parallel rotation axes at substantially same rotational speeds but in opposite senses of rotation,
   second synchronization means which constrain the two second rotary output members such that, in response to said staple actuating movement, the two second rotary output members rotate both contemporaneously with respect to said handle portion about parallel rotation axes at substantially same rotational speeds but in opposite senses of rotation.

5. A surgical instrument according to claim 4, wherein said anvil moving device comprises:
   two parallel arms extending proximally from the anvil and slidably received in two corresponding guide seats of the cartridge device;
   a first pair of moving screws received in a rotatably free but axially stationary manner in a proximal base structure of the staple fastening assembly, wherein distally extending threaded shafts of said moving screws fit into corresponding threaded holes formed inside the anvil arms such that a rotation of the moving screws causes the anvil to translate with respect to the cartridge device,
   each of said two moving screws being rotationally stiffly connected to respectively one of said two first rotary rods.

6. A surgical instrument according to claim 5, wherein said staple driving device comprises:
   a second pair of two driving screws received in a rotatably free but axially stationary manner in said proximal base structure of the staple fastening assembly and in thread-engagement with corresponding threaded holes defined in a pusher base such that a rotation of the driving screws causes the pusher base to translate with respect to the anvil and a cartridge containing the staples to expel the staples towards the anvil, each of said two driving screws being rotationally stiffly connected to respectively one of said two second rotary rods.

7. A surgical instrument according to claim 6, wherein the two anvil moving screws are arranged at two opposite lateral ends of the staple fastening assembly and the two staple driving screws are arranged side by side centrally between the anvil moving screws and define together with the latter a symmetrical screw pattern with respect to a longitudinal central plane of the curved staple fastening assembly.

8. A surgical instrument according to claim 4, comprising:
   a knife arranged inside the cartridge device and positioned along a side of at least one row of staples;
   a knife actuating device adapted to move the knife towards the anvil to cut the tissue clamped between the anvil and the cartridge device,
   said knife actuating device being coupled with said staple driving device.

9. A surgical instrument according to claim 3 or 4, wherein said synchronization means comprise a gear mechanism.

10. A surgical instrument according to claim 3, wherein the rotary rods are received inside flexible protective sheaths.

11. A surgical instrument according to claim 3, comprising a flexible elongate insertion shaft and connectors to connect the actuating transmission device to the insertion shaft.

* * * * *